(12) United States Patent
Dai et al.

(10) Patent No.: US 11,834,679 B2
(45) Date of Patent: Dec. 5, 2023

(54) METHOD FOR PRODUCING CARDIOMYOCYTES

(71) Applicants: KATAOKA CORPORATION, Kyoto (JP); Kyoto Prefectural Public University Corporation, Kyoto (JP)

(72) Inventors: Ping Dai, Kyoto (JP); Yukimasa Takeda, Kyoto (JP); Yoshinori Harada, Kyoto (JP); Junichi Matsumoto, Kyoto (JP); Ayumi Kusaka, Kyoto (JP)

(73) Assignees: Kataoka Corporation, Kyoto (JP); Kyoto Prefectural Public University Corporation, Kyoto (JP)

( * ) Notice: Subject to any disclaimer, the term of this patent is extended or adjusted under 35 U.S.C. 154(b) by 309 days.

(21) Appl. No.: 16/960,441

(22) PCT Filed: Jan. 24, 2019

(86) PCT No.: PCT/JP2019/002193
§ 371 (c)(1),
(2) Date: Jul. 7, 2020

(87) PCT Pub. No.: WO2019/151097
PCT Pub. Date: Aug. 8, 2019

(65) Prior Publication Data
US 2020/0354680 A1 Nov. 12, 2020

(30) Foreign Application Priority Data

Jan. 30, 2018 (JP) .................................. 2018-013301

(51) Int. Cl.
*C12N 5/077* (2010.01)

(52) U.S. Cl.
CPC .... *C12N 5/0657* (2013.01); *C12N 2506/1307* (2013.01)

(58) Field of Classification Search
CPC ...................... C12N 5/0657; C12N 2506/1307
See application file for complete search history.

(56) References Cited

U.S. PATENT DOCUMENTS

| | | | |
|---|---|---|---|
| 2013/0216503 A1 | 8/2013 | Srivastava et al. | |
| 2014/0301991 A1 | 10/2014 | Srivastava et al. | |
| 2016/0186141 A1 | 6/2016 | Cao et al. | |
| 2019/0071641 A1 | 3/2019 | Ieda et al. | |
| 2019/0218516 A1 | 7/2019 | Murakami et al. | |

FOREIGN PATENT DOCUMENTS

| | | | |
|---|---|---|---|
| JP | 2015-213441 A | 12/2015 | |
| JP | 2017-104091 A | 6/2017 | |
| WO | 2015/038704 A1 | 3/2015 | |
| WO | 2016/056438 A1 | 4/2016 | |

OTHER PUBLICATIONS

Lai (2017, Scientific Reports, 7:44534, pp. 1-13).*
Han (2016, Stem Cells International, vol. 2016, Article ID 4304916, pp. 1-11).*
Yang (2019, Stem Cell Reports, 13:862-876).*
Ichim (2018, Journal of Translational Medicine, 16:212, pp. 1-9).*
Grath (2019, Journal of Biological Engineering, 13: pp. 1-15).*
Grotheer (2021, Scientific Reports, 11:11968, 17 pages).*
The International Bureau of WIPO, "International Preliminary Report on Patentability," issued in International Application No. PCT/JP2019/002193, of which U.S. Appl. No. 16/960,441 is a U.S. national phase entry, dated Aug. 4, 2020, 16 pages (9 pages of English translation of International Preliminary Report on Patentability and 7 pages of original International Preliminary Report on Patentability).
Nan Cao et al., "Conversion of human fibroblasts into functional cardiomyocytes by small molecules," Science, vol. 352, Issue 6290, Jun. 3, 2016, pp. 1216-1220, [online] <https://science.sciencemag.org/>, retrieved Jun. 22, 2020.
Ping Dai et al., "Direct Reprogramming by Small Molecules for Regenerative Medicine," Journal of Kyoto Prefectural University of Medicine, vol. 127, No. 1, 2018, pp. 1-12.
Ping Dai et al., "Highly Efficient Direct Conversion of Human Fibroblasts to Neuronal Cells by Chemical Compounds," Journal of Clinical Biochemistry and Nutrition, vol. 56, No. 3, May 2015, pp. 166-170.
Yanbin Fu et al., "Direct reprogramming of mouse fibroblasts into cardiomyocytes with chemical cocktails," Cell Research, vol. 25, No. 9, 2015, pp. 1013-1024, Nature Publishing Group.
Paul W. Burridge et al., "Production of De Novo Cardiomyocytes: Human Pluripotent Stem Cell Differentiation and Direct Reprogramming," Cell Stem Cell, vol. 10, pp. 16-28, Jan. 6, 2012, Elsevier Inc.
Shangtao Cao et al., "Chemical reprogramming of mouse embryonic and adult fibroblast into endoderm lineage," Journal of Biological Chemistry, vol. 292, No. 46, pp. 19122-19132, 2017.
Amanda W. Smith et al., "Direct reprogramming of mouse fibroblasts to cardiomyocyte-like cells using Yamanaka factors on engineered poly(ethylene glycol) (PEG) hydrogels," Biomaterials, vol. 34, pp. 6559-6571, 2013.

* cited by examiner

*Primary Examiner* — Valarie E Bertoglio
(74) *Attorney, Agent, or Firm* — Morgan, Lewis & Bockius LLP

(57) ABSTRACT

The present invention chiefly aims to provide a process for directly inducing cardiomyocytes from somatic cells without performing artificial gene transfer, a cardiomyocyte obtained thereby, and a composition comprising a combination of chemical compounds capable of using for the said process. The present invention can include a process for producing a cardiomyocyte by inducing differentiation directly from a somatic cell, the process comprising a step of culturing the somatic cell in the presence of a MEK inhibitor and a cAMP inducer, and a cardiomyocyte obtained thereby, and then a composition for producing a cardiomyocyte by inducing differentiation directly from a somatic cell, the composition comprising a MEK inhibitor and a cAMP inducer. The cardiomyocytes obtained according to the present invention are useful in regenerative medicine and the like.

8 Claims, 8 Drawing Sheets

[Figure 1]
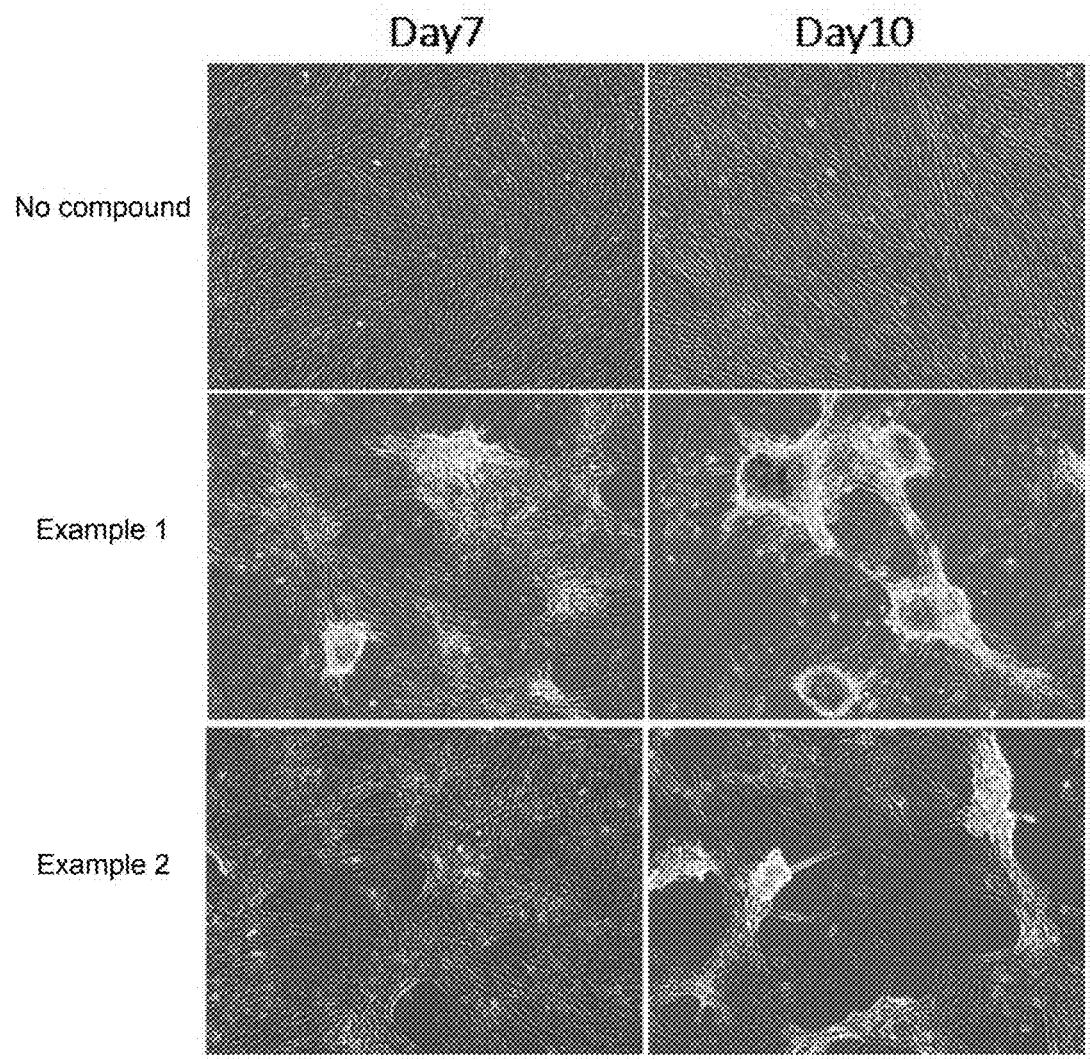

[Figure 2]
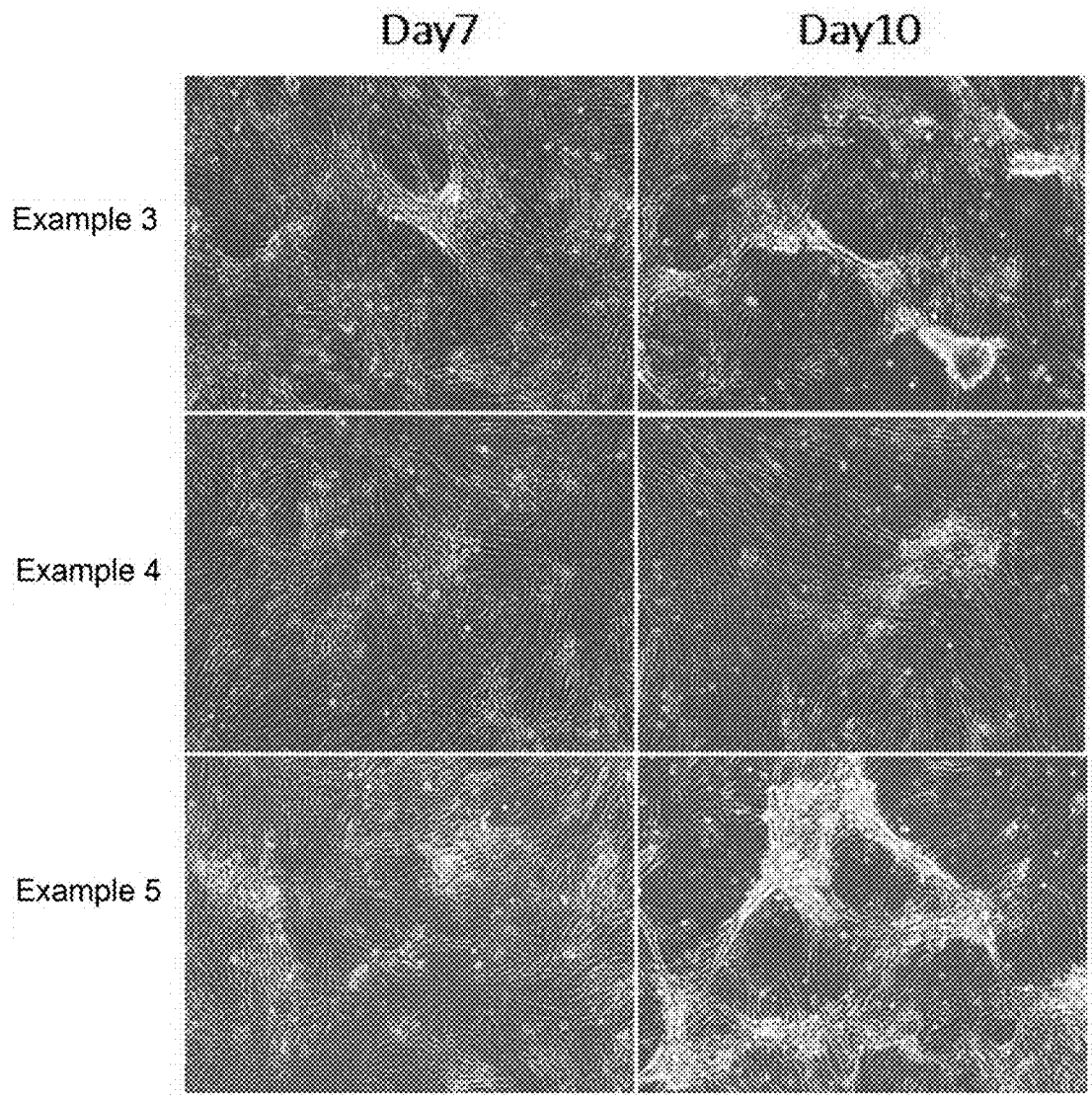

[Figure 3]
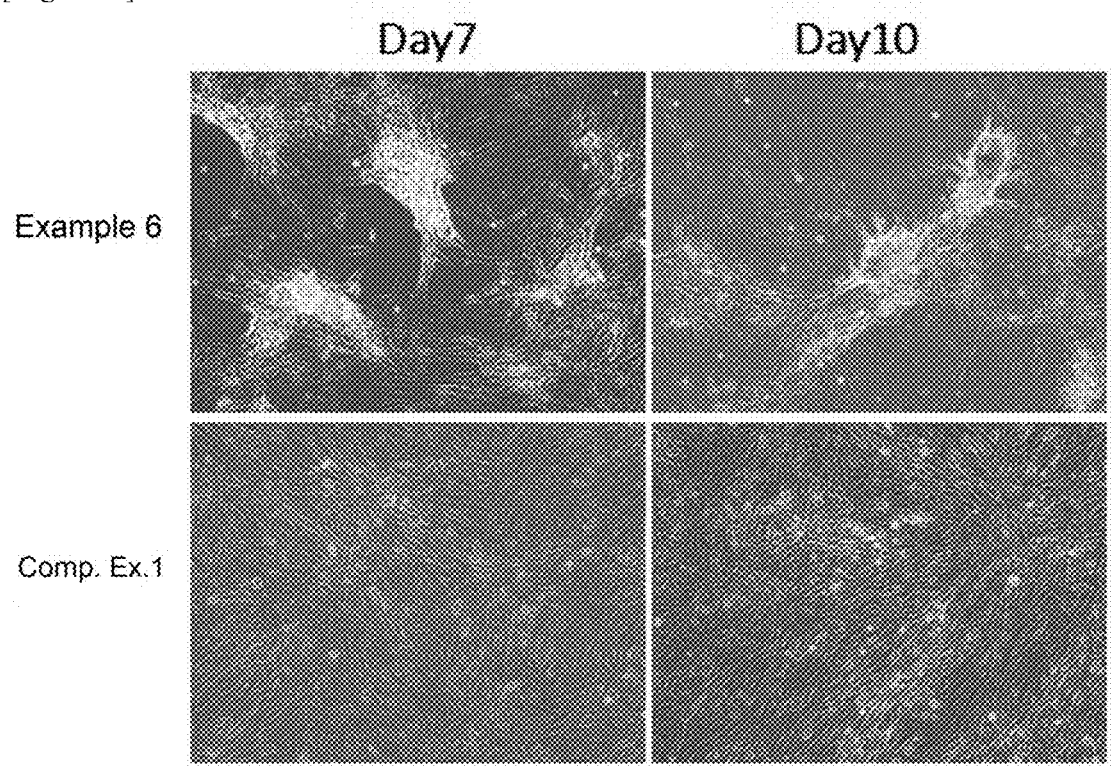

[Figure 4]
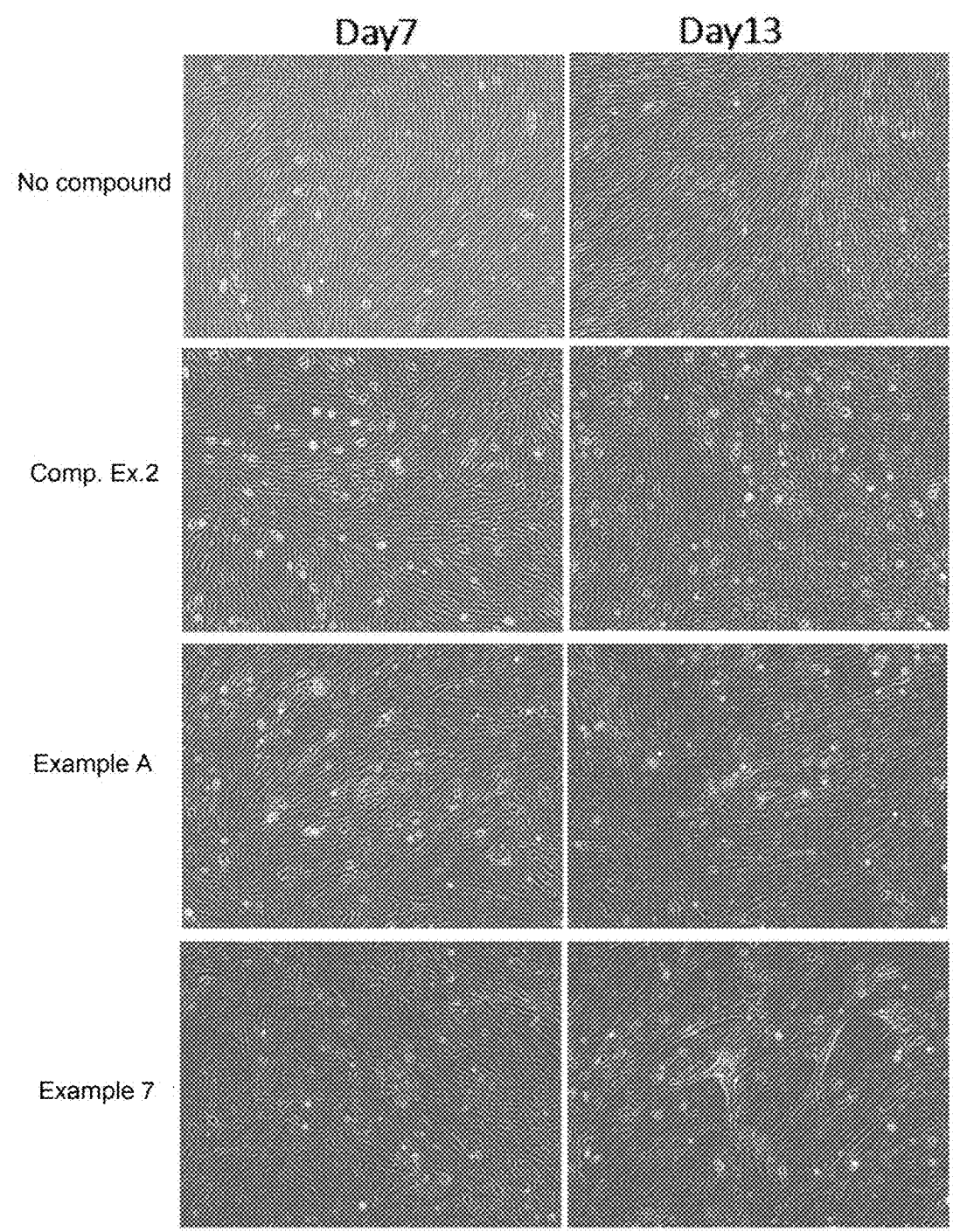

[Figure 5]
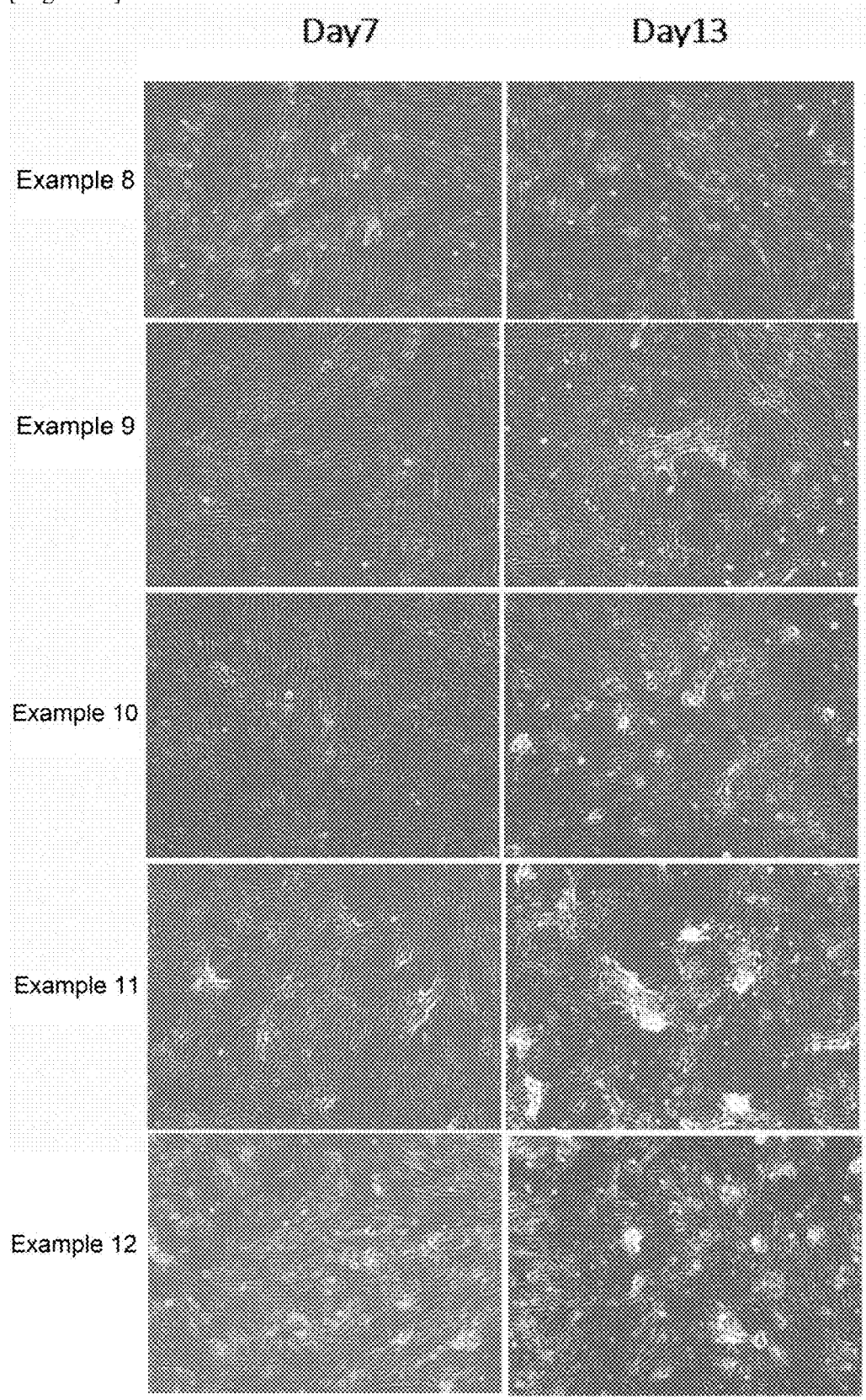

[Figure 6]
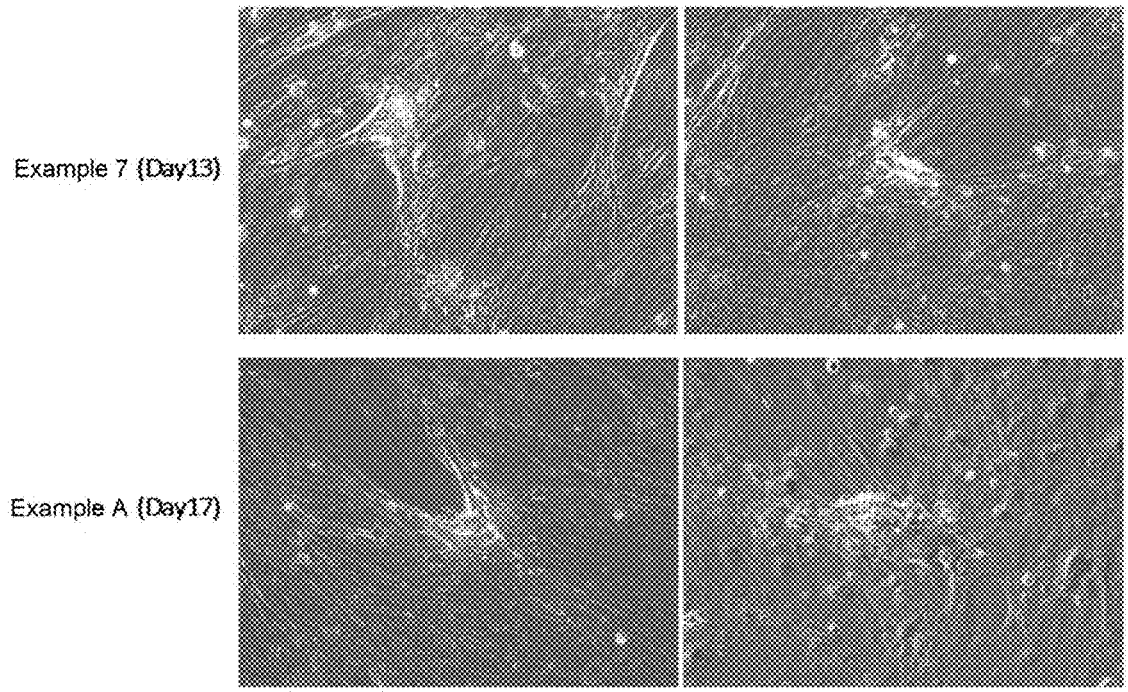
[Figure 7]
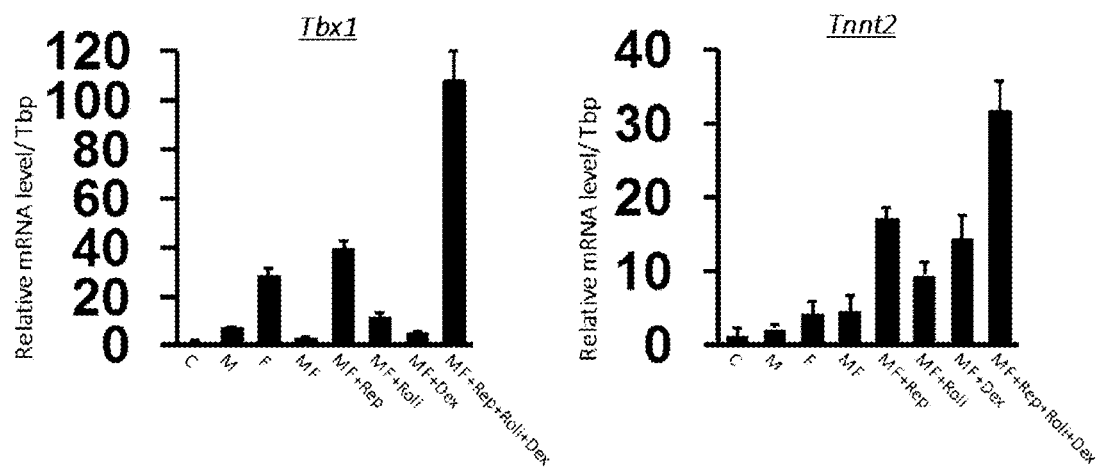

[Figure 8]
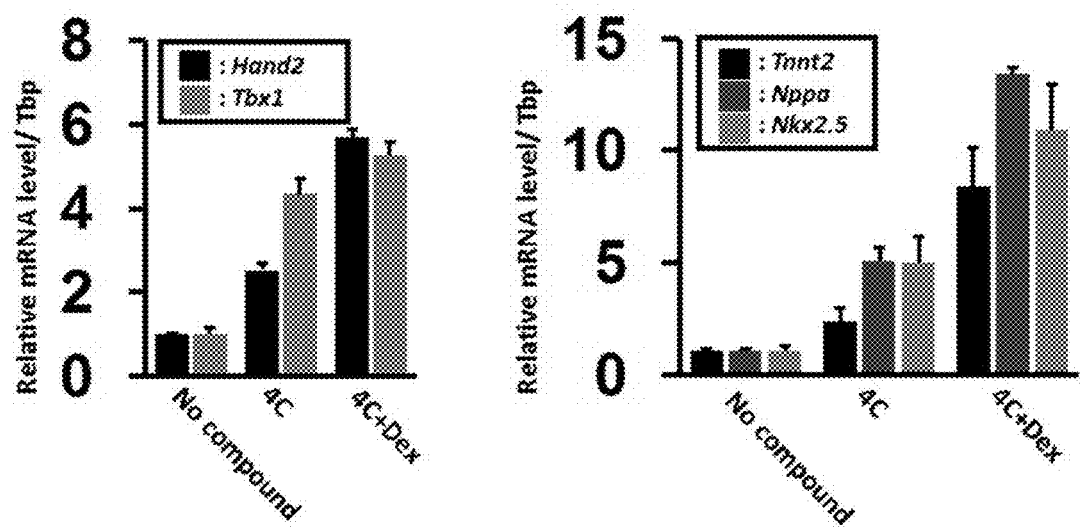
[Figure 9]
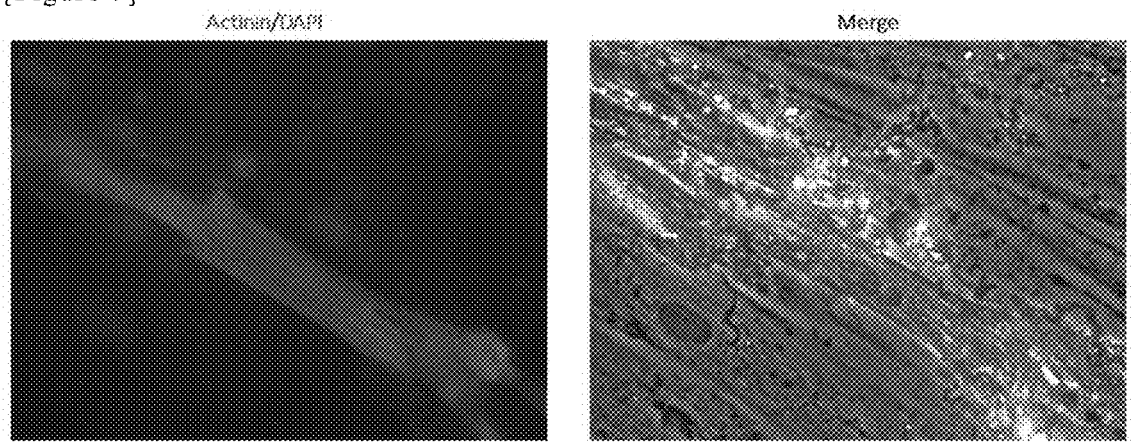

[Figure 10]
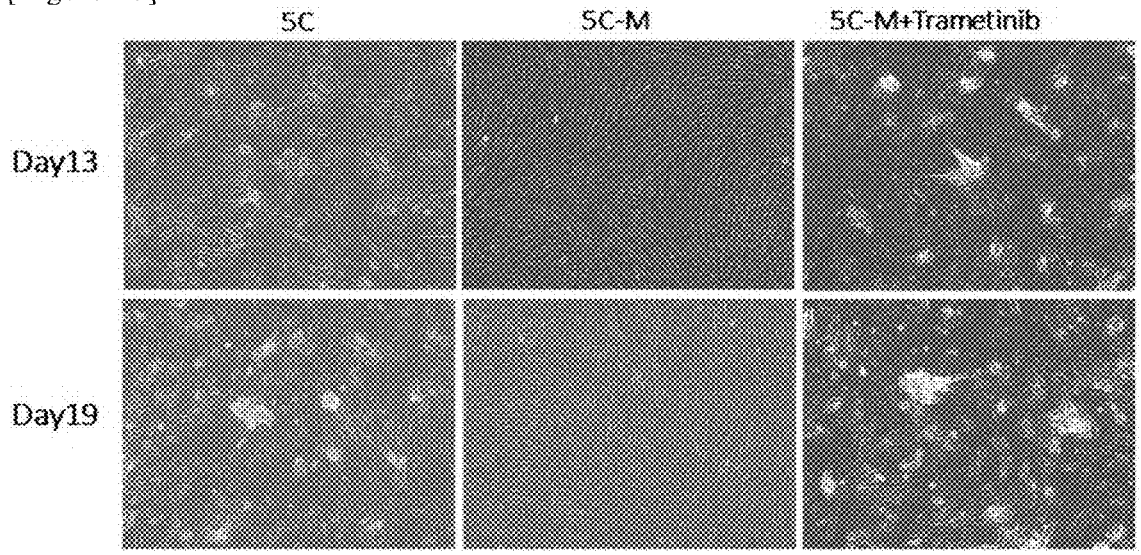
[Figure 11]
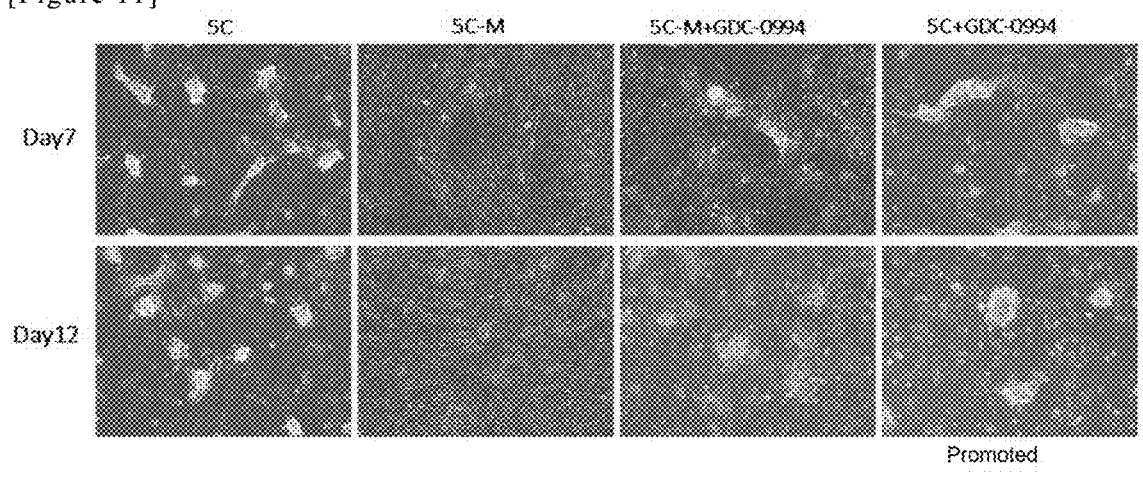

US 11,834,679 B2

METHOD FOR PRODUCING CARDIOMYOCYTES

TECHNICAL FIELD

Cross-Reference of Related Applications

This application claims priority from Japanese Application No. 2018-13301, filed Jan. 30, 2018, the disclosure of which is incorporated herein in its entirety.

The present invention belongs to the field of regenerative medicine or direct reprogramming from somatic cells. The present invention relates in the field to a process for direct production of cardiomyocytes from somatic cells by low molecular weight compounds, and to low molecular weight compound inducible cardiomyocytes (ciCMs: chemical compound induced-Cardiomyocytes) produced by such a process. The present invention further relates to such cardiomyocytes and compositions that can be used for processes of producing such cardiomyocytes.

BACKGROUND OF THE INVENTION

Recent developments in cell-related research, particularly in pluripotent cells, have made it possible to obtain therapeutic cells in the quality and quantity available for transplantation into an individual. For several diseases, attempts have been initiated to transplant cells that are effective for treatment into patients.

The cells of the mesenchymal system form various organs of the living body such as muscle, bone, cartilage, bone marrow, fat and connective tissue, and are promising as materials of regenerative medicine. Mesenchymal stem cells (MSCs) are undifferentiated cells present in tissues such as bone marrow, adipose tissue, blood, placentas and umbilical cord. Because of their ability to differentiate into cells belonging to the mesenchymal system, mesenchymal stem cells have attracted attention as a starting material in the production of these cells. Regenerative medicine using mesenchymal stem cells themselves for reconstruction of bone, cartilage, myocardium, etc. is also being investigated.

Meanwhile, methods have also been reported to convert somatic cells such as fibroblasts directly into other cells. For example, it is known to obtain a neural cell by cultivating the fibroblast with a chemical substance (Non-Patent Document 1).

Cardiomyocytes are also known to be induced directly from murine fetal fibroblasts by culturing with certain chemicals including GSK3 inhibitors (CHIR99021) and the like (Non-Patent Document 2). Similarly, it is known to be derived directly from human foreskin fibroblasts (HFF) or fetal lung fibroblasts (HLF) (Non-Patent Document 3).

Further, Patent Document 1 describes an invention for directly inducing cardiac muscle cells from human fibroblasts by a composition comprising at least five selected from a WNT agonist, a GSK3 inhibitor, a TGF-β inhibitor, an extracellular signal regulating kinase (ERK1), a Ras GTPase active protein inhibitor (Ras-GAP), an Oct-4 activator, a Rho-related coiled coil-forming protein serine/threonine kinase inhibitor, an iron chelator, a KDM5B inhibitor, a histone methyl transfer agent, and a PDGF tyrosine kinase inhibitor. Patent Document 2 describes an invention for directly inducing a cardiac muscle cell from a human fibroblast by cultivating the somatic cells, in the presence of at least one inhibitor selected from the group consisting of an ALK6 inhibitor and an AMPK inhibitor, and in the presence of a cAMP activator, an ALK5 inhibitor (a TGF-β inhibitor) and an ERK inhibitor.

PRIOR ART

Patent Document

Patent Document 1: U.S. Patent Application Publication No. 2016/0186141
Patent Document 2: International Publication No. 2018/062269

Non-Patent Document

Non-Patent Document 1: Journal of Clinical Biochemistry and Nutrition, 2015, Vol. 56, No. 3, pp. 166-170
Non-Patent Document 2: Cell Research, 2015, 25, 1013-1024
Non-Patent Document 3: Science, 2016, 352, 1216-1220

SUMMARY OF THE INVENTION

Problem to be Solved by the Present Invention

As in the method described in Non-Patent Document 1, a method of directly converting a somatic cell into a desired cell without gene transfer may be an effective option as a means of obtaining a therapeutic cell. As described above, cardiomyocytes are actually directly induced by culturing with a certain chemical substance, but in the invention described in Non-Patent Document 2, they are directly induced from mouse fibroblasts and not directly induced from human fibroblasts. In the invention described in Non-Patent Document 3, cardiomyocytes are directly derived from human fibroblasts, and a supernatant of cardiomyocytes differentiated from ES cells is indispensable for this. In the inventions described in Patent Documents 1 and 2, cardiomyocytes are directly derived from human fibroblasts.

It is a main object of the present invention to provide a process for directly inducing cardiomyocytes from somatic cells without performing artificial gene transfer and by a combination of low molecular weight compounds different from those described in Patent Documents 1 and 2, that is, a new process capable of directly producing cardiomyocytes from somatic cells by a composition of certain low molecular weight compounds.

Means for Solving the Problems

As a result of intensive studies, the present inventors have found that somatic cells can be directly converted into cardiomyocytes by culturing the somatic cells in the presence of a certain small molecule inhibitor or the like, and have thus completed the present invention.

The present invention can include the following, for example.

[1] A process for producing a cardiomyocyte by inducing differentiation directly from a somatic cell, the process comprising a step of culturing the somatic cell in the presence of a MEK inhibitor.
[2] The process for producing a cardiomyocyte according to the above [1], wherein the said step is a step of culturing the somatic cell in the further presence of a cAMP inducer.
[3] The process for producing a cardiomyocyte according to the above [1] or [2], wherein the said step is a step of culturing the somatic cell in the further presence of at least one member selected from the group consisting of a TGF-β inhibitor, a PDE4 inhibitor, and a GR agonist.

[4] The process for producing a cardiomyocyte according to the above [3], wherein the said step is a step of culturing the somatic cell in the further presence of an ERK inhibitor.

[5] The process for producing a cardiomyocyte according to any one of the above [1] to [3], wherein the said step is a step of culturing the somatic cell in the presence of any combination of the following items (1) to (6);
(1) a MEK inhibitor, a cAMP inducer, and a TGF-β inhibitor,
(2) a MEK inhibitor, a cAMP inducer, and a PDE4 inhibitor,
(3) a MEK inhibitor, a cAMP inducer, and a GR agonist,
(4) a MEK inhibitor, a cAMP inducer, a PDE4 inhibitor, and a GR-agonist,
(5) a MEK inhibitor, a cAMP inducer, a TGF-β inhibitor, a PDE4 inhibitor, and a GR agonist,
(6) a MEK inhibitor, a cAMP inducer, a TGF-β inhibitor, a PDE4 inhibitor, a GR agonist, and an ERK inhibitor.

[6] The process for producing a cardiomyocyte according to any one of the above [1] to [5], wherein the said step is a step of culturing the somatic cell in the further presence of at least one member selected from the group consisting of a RAR agonist, an RXR agonist, and a PDK1 activator.

[7] The process for producing a cardiomyocyte according to any one of the above [1] to [6], wherein the MEK inhibitor is PD0325901.

[8] The process for producing a cardiomyocyte according to any one of the above [2] to [7], wherein the cAMP inducer is forskolin.

[9] The process for producing a cardiomyocyte according to any one of the above [3] to [8], wherein the TGF-β inhibitor is RepSox, the PDE4 inhibitor is rolipram, or the GR agonist is dexamethasone.

[10] The process for producing a cardiomyocyte according to any one of the above [4] to [9], wherein the ERK inhibitor is GDC-0994.

[11] A process for producing a cardiomyocyte by inducing differentiation directly from a somatic cell, the process comprising a step of culturing the somatic cell in the presence of a cAMP inducer, a TGF-β inhibitor, a PDE4 inhibitor, a GR agonist, and an ERK inhibitor.

[12] The process for producing a cardiomyocyte according to the above [11], wherein the cAMP inducer is forskolin, the TGF-β inhibitor is RepSox, the PDE4 inhibitor is rolipram, the GR agonist is dexamethasone, or the ERK inhibitor is GDC-0994.

[13] The process for producing a cardiomyocyte according to any one of the above [1] to [12], wherein the somatic cell is a fibroblast.

[14] A cardiomyocyte produced from the process for producing a cardiomyocyte according to any one of the above [1] to [13].

[15] A composition for producing a cardiomyocyte by inducing differentiation directly from a somatic cell, the composition comprising a MEK inhibitor.

[16] The composition according to the above [15], further comprising a cAMP inducer.

[17] The composition according to the above [15] or [16], further comprising at least one member selected from the group consisting of a TGF-β inhibitor, a PDE4 inhibitor, and a GR agonist.

[18] The composition of the above [17], further comprising an ERK inhibitor.

[19] The composition of any one of the above [15] to [18], comprising any combination of the following items (1) to (6);
(1) a MEK inhibitor, a cAMP inducer, and a TGF-β inhibitor,
(2) a MEK inhibitor, a cAMP inducer, and a PDE4 inhibitor,
(3) a MEK inhibitor, a cAMP inducer, and a GR agonist,
(4) a MEK inhibitor, a cAMP inducer, a PDE4 inhibitor, and a GR-agonist,
(5) a MEK inhibitor, a cAMP inducer, a TGF-β inhibitor, a PDE4 inhibitor, and a GR agonist,
(6) a MEK inhibitor, a cAMP inducer, a TGF-β inhibitor, a PDE4 inhibitor, a GR agonist, and an ERK inhibitor.

[20] The composition according to any one of the above [15] to [19], further comprising at least one member selected from the group consisting of a RAR agonist, an RXR agonist, and a PDK1 activator.

[21] The composition of any one of the above [15] to [20], wherein the MEK inhibitor is PD0325901.

[22] The composition of any one of the above [16] to [21], wherein the cAMP inducer is forskolin.

[23] The composition according to any one of the above [17] to [22], wherein the TGF-β inhibitor is RepSox, the PDE4 inhibitor is rolipram, or the GR agonist is dexamethasone.

[24] The composition of any one of the above [18] to [23], wherein the ERK inhibitor is GDC-0994.

[25] A composition for producing a cardiomyocyte by inducing differentiation directly from a somatic cell, the composition comprising a cAMP inducer, a TGF-β inhibitor, a PDE4 inhibitor, a GR agonist, and an ERK inhibitor.

[26] The composition according to the above [25], wherein the cAMP inducer is forskolin, the TGF-β inhibitor is RepSox, the PDE4 inhibitor is rolipram, the GR agonist is dexamethasone, or the ERK inhibitor is GDC-0994.

[27] The composition of any one of the above [15] to [26], wherein the somatic cell is a fibroblast.

Effect of the Invention

According to the present invention, it is possible to produce spontaneously beating cardiomyocytes from somatic cells without gene transfer. The cardiomyocytes obtained according to the present invention are useful in regenerative medicine and the like.

BRIEF DESCRIPTION OF THE DRAWINGS

FIG. 1 is culture photographs of cells. In each photograph, the left side shows the result on the $7^{th}$ day of culture, and the right side shows the result on the $10^{th}$ day after the start of culturing.

FIG. 2 is culture photographs of cells. In each photograph, the left side shows the results on the $7^{th}$ day of culturing and the right side shows the results on the $10^{th}$ day of culturing.

FIG. 3 is culture photographs of cells. In each photograph, the left side shows the results on the $7^{th}$ day of culturing and the right side shows the results on the $10^{th}$ day of culturing.

FIG. 4 is culture photographs of cells. In each photograph, the left side shows the results on the $7^{th}$ day of culturing and the right side shows the results on the $13^{th}$ day of culturing.

FIG. 5 is culture photographs of cells. In each photograph, the left side shows the results on the 7$^{th}$ day of culturing and the right side shows the results on the 13$^{th}$ day of culturing.

FIG. 6 is culture photographs of cells. The top two show the results on the 13$^{th}$ day of culturing at different points for Example 7 and the bottom two show the results on the 17$^{th}$ day of culturing at different points for Example A, respectively.

FIG. 7 shows relative expression levels of mRNA. The left figure shows the expression amount of the myocardial progenitor cell specific gene Tbx1 by each combination inhibitor and the like, and the right figure shows the expression amount of the myocardial cell specific gene Tnnt2 by each combination inhibitor and the like, respectively. In the figures, the vertical axis represents the relative value of mRNA amount relative to the internal standard gene amount (Tbp).

FIG. 8 shows relative expression levels of mRNA. The left figure shows the expression amount of the myocardial progenitor cell specific gene by each combination inhibitor, etc., and the right figure shows the expression amount of the myocardium specific gene by each combination inhibitor, etc. In the figures, the vertical axis represents the relative value of mRNA amount relative to the internal standard gene amount (Tbp).

FIG. 9 is immunostaining photographs of cells, wherein the left is one stained with Alpha Actinin/DAPI and the right is one in which a bright field image is superimposed on the left one.

FIG. 10 is culture photographs of cells. The top three photographs show the results on the 13$^{th}$ day of culturing, and the bottom three photographs show the results on the 19$^{th}$ day of culturing, respectively.

FIG. 11 is culture photographs of cells. The top four photographs show the results on the 7$^{th}$ day of culturing, and the bottom four photographs show the results on the 12$^{th}$ day of culturing, respectively.

EMBODIMENT FOR CARRYING OUT THE PRESENT INVENTION

Hereinafter is described about the present invention in detail.

1 Process for Producing a Cardiomyocyte

The process for producing a cardiomyocyte, according to the present invention (hereinafter referred to as the "present invention process"), is a process for producing a cardiomyocyte by inducing differentiation directly from a somatic cell, characterized by comprising a step of culturing the somatic cell in the presence of a MEK-inhibitor.

In the present invention process, the above-mentioned step can preferably include one that cultures the somatic cell in the further presence of a cAMP inducer. More preferably, in the present invention process, the above-mentioned step can include one that cultures the somatic cell in the further presence of at least one member selected from the group consisting of a TGF-β inhibitor, a PDE4 inhibitor, and a GR agonist. Still more preferably, in the present invention process, the above-mentioned step can include one that cultures the somatic cell in the further presence of an ERK inhibitor. Particularly preferred is the present invention process, wherein the above-mentioned step is a step of culturing the somatic cell in the presence of any combination of the following items (1) to (6);

(1) a MEK inhibitor, a cAMP inducer, and a TGF-β inhibitor, (2) a MEK inhibitor, a cAMP inducer, and a PDE4 inhibitor, (3) a MEK inhibitor, a cAMP inducer, and a GR agonist, (4) a MEK inhibitor, a cAMP inducer, a PDE4 inhibitor, and a GR-agonist, (5) a MEK inhibitor, a cAMP inducer, a TGF-β inhibitor, a PDE4 inhibitor, and a GR agonist, (6) a MEK inhibitor, a cAMP inducer, a TGF-β inhibitor, a PDE4 inhibitor, a GR agonist, and an ERK inhibitor.

The present invention also includes a process for producing a cardiomyocyte by inducing differentiation directly from a somatic cell, the process comprising a step of culturing the somatic cell in the presence of a cAMP inducer, a TGF-β inhibitor, a PDE4 inhibitor, a GR agonist, and an ERK inhibitor. Hereinafter, such a process is also referred to as the present invention process.

In the above step of the present invention process, the somatic cell can be cultured in the further presence of at least one member selected from the group consisting of a RAR agonist, an RXR agonist, and a PDK1 activator.

In the present invention process, the somatic cell may be cultured in the presence of at least any combination of the above, and the somatic cell may optionally be cultured in the presence of other inhibitors, inducers, or the like to produce a cardiomyocyte, if necessary.

Each of the above inhibitors, inducers, and the like may be alone or a combination of two or more kinds.

Specific inhibitors and the like may have two or more kinds of inhibitory effects, and in this case, one inhibitor and the like may be considered to include a plurality of inhibitors and the like.

1.1 Somatic Cells

Cells of an organism can be classified into somatic and germ cells. Any somatic cell can be used as a starting material in the process of the present invention. The somatic cell is not particularly limited, and may be either a primary cell taken from a living body or a cell that has been strained. Somatic cells at various stages of differentiation, e.g., terminally differentiated somatic cells (e.g., fibroblasts, umbilical vein endothelial cells (HUVEC), hepatocellulars (Hepatocytes), bile duct cells (Biliary cells), pancreatic alpha cells (Pancreatic a cells), pancreatic acinar cells (Acinar cells), pancreatic ductal gland cells (Ductal cells), small intestinal crypt cells (Intestinal crypt cells), etc.), somatic cells on the way to terminal differentiation (e.g., mesenchymal stem cells, neural stem cells, endodermal progenitor cells, etc.), or initialized and pluripotent somatic cells can be used. The somatic cells that can be used in the method of the present invention include any somatic cells, for example, cells of the hematopoietic system (various lymphocytes, macrophages, dendritic cells, bone marrow cells, etc.), cells derived from organs (hepatocellulars, splenocytes, pancreatic cells, kidney cells, lung cells, etc.), cells of the muscle tissue system (skeletal muscle cells, smooth muscle cells, myoblasts, cardiomyocytes, etc.), fibroblasts, nerve cells, osteoblasts, chondrocytes, endothelial cells, interstitial cells, adipocytes (brown adipocytes, white adipocytes, etc.), and the like. The method of the present invention can also be applied to precursor cells and cancer cells of these cells. Preferably, fibroblasts can be used.

Examples of the source of the above-mentioned somatic cells include, but are not limited to, humans, non-human mammals, and non-mammals (birds, reptiles, amphibians, fish, etc.). As the source of the somatic cells, humans and non-human mammals are preferable, and humans are particularly preferable. When cardiomyocytes are produced by the present invention process for administration to humans, preferably somatic cells harvested from a donor that matches or is similar to the type of histocompatibility antigen with the recipient can be used. Somatic cells harvested from the recipient itself may be used for the production of cardiomyocytes.

1.2 Inhibitors, Etc. According to the Present Invention
2.1 MEK Inhibitors

MEK (MAPK/ERK kinases) is a phosphoenzyme belonging to MAPK signaling pathway activated by growth factors such as EGFs (epidermal growth factors), and in mammals, there is MEK1 and MEK2 encoded by two genes. MEK is phosphorylated by an upstream RAF, which activates MEK to signal further downstream by phosphorylating ERK. Inhibition of ERK phosphorylation by MEK inhibitors blocks the MEK-mediated MAPK signaling pathway.

The term "in the presence of a MEK inhibitor" means under a culture condition capable of inhibiting MEK, preferably MEK1 or MEK2, and the means thereof is not particularly limited, and substances that inhibit the activity of MEK, for example, MEK signal inhibiting means such as anti-MEK antibodies or MEK inhibitors can be used. Means for inhibiting proteins involved in the activation of MEK, e.g., enzyme-membrane receptors such as EGFR located upstream of MEK in MAPK signaling pathway, small GTP-binding proteins RAS, phosphorylase RAFs, etc., can also be used for MEK inhibition.

Although not particularly limited in the present invention, as the MEK inhibitor, for example, the following compounds can be used. Preferably, PD0325901, Trametinib can be used.

PD0325901 (CAS No.:391210-10-9)

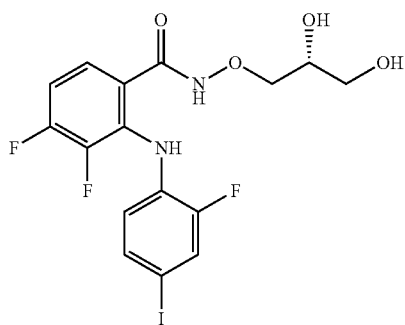

[Chemical 1]

Trametinib (CAS No.: 871700-17-3)

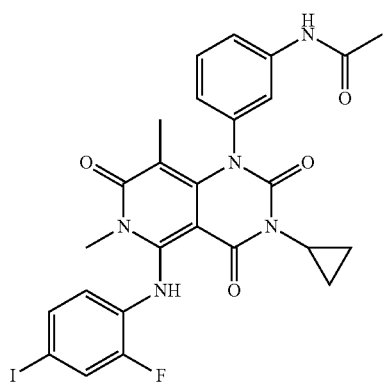

[Chemical 2]

U0126-EtOH (CAS No.: 1173097-76-1)
TAK-733 (CAS No.: 1035555-63-5)
BI-847325 (CAS No.: 1207293-36-4)
Honokiol (CAS No.: 35354-74-6)
Myricetin (CAS No.: 529-44-2)
AS703026 (CAS No.: 1236699-92-5)
AZD8330 (CAS No.: 869357-68-6)
CI-1040 (CAS No.: 212631-79-3)
Cobimetirlib (CAS No.: 934660-93-2)
GDC-0623 (CAS No.: 1168091-68-6)
MEK162 (CAS No.: 606143-89-9)
PD318088 (CAS No.: 391210-00-7)
PD98059 (CAS No.: 167869-21-8)
Refametinib (CAS No.: 923032-37-5)
Selumetinib (CAS No.: 606143-52-6)
SL327 (CAS No.: 305350-87-2)

The concentration of the MEK inhibitor may be appropriately determined, and is not particularly limited, and may be used, for example, in the range of 0.1 µmol/L to 10 µmol/L, preferably 0.5 µmol/L to 5 µmol/L.

1.2.2 cAMP Inducers cAMP (cyclic Adenosine Monophosphate) is a second messenger that is involved in a variety of intracellular signaling events. cAMP is produced intracellularly by cyclization of adenosine triphosphate (ATP) by adenylyl cyclase (adenylate cyclase).

The term "in the presence of a cAMP inducer" means under a culture condition capable of inducing cAMP, and the means thereof is not particularly limited, and any means capable of increasing intracellular cAMP concentrations, for example, can be used. Substances that can induce it by direct action on adenylate cyclase, which is an enzyme involved in the production of cAMP, substances that can promote the expression of adenylate cyclase, and substances that inhibit phosphodiesterase, which is an enzyme that degrades cAMP, can be used as means for increasing intracellular cAMP concentrations. Membrane permeable cAMP analogues such as dibutyryl cAMP or 8-bromo-cAMP, which are structural analogues of cAMP that have the same effect as cAMP in cells, can also be used.

Although not particularly limited in the present invention, the cAMP inducer (adenylate cyclase activating agents) can include forskolin (CAS No.: 66575-29-9), forskolin derivatives (for example, Japanese Patent Laid-Open No. 2002-348243), the following compounds, and the like. Preferably, forskolin can be used.

Forskolin (CAS No.: 66428-89-5)

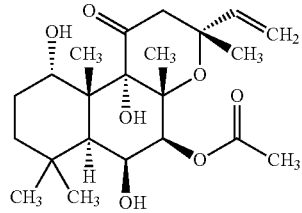

[Chemical 3]

Isoproterenol (CAS No.: 7683-59-2)
NKH477 (CAS No.: 138605-00-2)
PACAP1-27 (CAS No.: 127317-03-7)
PACAP1-38 (CAS No.: 137061-48-4)

The concentration of the cAMP inducer may be appropriately determined, and is not particularly limited, and may be used, for example, in the range of 0.2 µmol/L to 50 µmol/L, preferably 1 µmol/L to 30 µmol/L.

1.2.3 TGF-β Inhibitors

There are three types of TGF-β (transforming growth factor-β), TGF-β1, TGF-β2, and TGF-β3, which are produced from almost all cells. TGF-β is involved in a wide variety of cellular functions, including cell growth, transformation, differentiation, development, and control of apoptosis, such as suppressing the growth of epithelial cells and many other cells.

The term "in the presence of a TGF-β inhibitor" means under a culture condition capable of inhibiting TGF-β, and the means thereof is not particularly limited, and any means capable of inhibiting TGF-β can be used. Substances that act directly on TGF-β to inhibit its function (e.g., anti TGF-β antibodies and other drugs), agents that inhibit the production of TGF-β themselves, or the like can be used in the present invention. TGF-β can also be inhibited by inhibiting signaling that involves TGF-β upstream.

Although not particularly limited in the present invention, as the TGF-β inhibitor, for example, the following compounds can be used. Preferably, RepSox can be used.
A83-01 (CAS No.: 909910-43-6)

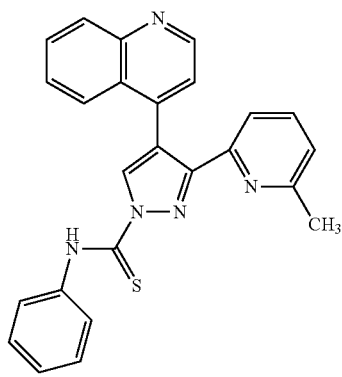

[Chemical 4]

RepSox (CAS No.: 446859-33-2)

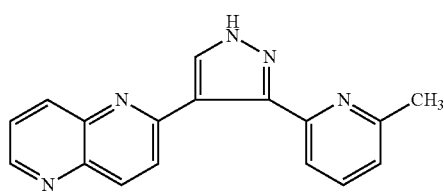

[Chemical 5]

SB431542 (CAS No.: 301836-41-9)

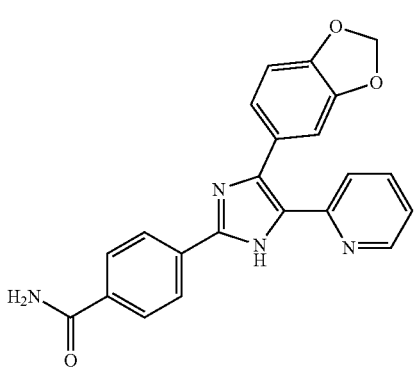

[Chemical 6]

LY364947 (CAS No.: 396129-53-6)
SB525334 (CAS No.: 356559-20-1)
SD208 (CAS No.: 627536-09-8)
Galunisertib (LY2157299) (CAS No.: 700874-72-2)
LY2109761 (CAS No.: 700874-71-1)
SB505124 (CAS No.: 694433-59-5)
GW788388 (CAS No.: 452342-67-5)
EW-7197 (CAS No.: 1352608-82-2)

The concentration of the TGF-β inhibitor may be appropriately determined, and is not particularly limited, and may be used, for example, in the range of 0.1 μmol/L to 30 μmol/L, preferably in the range of 0.5 μmol/L to 10 μmol/L.

1.2.4 PDE4 Inhibitors

PDE4 (Phosphodiesterase-4) is one of the phosphodiesterase superfamilies. Phosphodiesterases are enzymes that hydrolyze phosphate diester bonds, particularly PDE4, which hydrolyzes cyclic phosphate diester bonds in cAMP, a second messenger of signaling pathways, and plays a crucial role in regulating their intracellular concentrations. PDE4 is present in immune cells, brain and nervous cells, etc.

The term "in the presence of a PDE4 inhibitor" means under a culture condition capable of inhibiting PDE4, and the means thereof is not particularly limited, and any means capable of inhibiting PDE4 can be used. Substances that act directly on PDE4 to inhibit its function (e.g., anti PDE4 antibodies and other drugs), agents that inhibit the production of PDE4 per se, or the like can be used in the present invention. PDE4 can also be inhibited by inhibiting PDE4 signaling upstream.

Although not particularly limited in the present invention, as the PDE4 inhibitor, for example, the following compounds can be used. Preferably, a rolipram or its optical isomer (e.g., R(−) or S(+) body) can be used.
Rolipram (CAS No.: 61413-54-5)

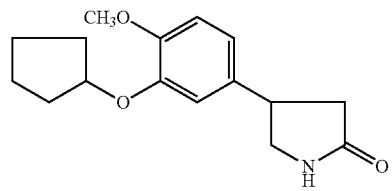

[Chemical 7]

Roflumilast (CAS No.: 162401-32-3)
Cilomilast (CAS No.: 153259-65-5)
GSK256066 (CAS No.: 801312-28-7)
Apremilast (CC-10004) (CAS No.: 608141-41-9)

The concentration of the PDE4 inhibitor may be appropriately determined, and is not particularly limited, and may be used, for example, in the range of 0.1 μmol/L to 20 μmol/L, preferably in the range of 0.5 μmol/L to 10 μmol/L.

1.2.5 GR Agonists

GR (Glucocorticoid Receptor) belongs to the nuclear receptor superfamily and serves as transcription factors that bind the steroid hormone glucocorticoids to regulate their transcriptional activity. The GR is widely expressed throughout the human body, and due to its functional importance, numerous synthetic agonists such as dexamethasone have been developed.

The term "in the presence of a GR agonist" means under a culture condition capable of activating GR, and the means thereof is not particularly limited, and any means capable of activating GR can be used. Substances that act directly on GR to operate its function, agents that promote expression of GR itself, or the like can be used in the present invention. It can also control GR function by regulating transcription factors or transcription coupling factors that interact with GR, as well as their expression and post-translational modifications.

Although not particularly limited in the present invention, as the GR agonist, for example, the following compounds can be used. Preferably, dexamethasone can be used.

Steroidal compounds such as dexamethasone, betamethasone, prednisolone, prednisone, methylprednisolone, triamcinolone, beclomethasone, budesonide, hydrocortisone, cortisone acetate, GSK9027, fluticasone and mometasone. Nonsteroidal compounds classified as selective glucocorticoid receptor modifiers or selective glucocorticoid receptor agonists.

The concentration of the GR agonist may be appropriately determined, and is not particularly limited, and may be used, for example, in the range of 0.01 µmol/L to 10 µmol/L, preferably 0.05 µmol/L to 2 µmol/L.

1.2.6 RAR Agonists, RXR Agonists

RAR (Retinoic acid receptor, retinoic acid receptor) belongs to the nuclear receptor superfamily and is liganded by retinoic acid, and its transcriptional activity is activated. Since RAR has various functions in vivo and is closely related to cell differentiation in particular, a number of artificial synthetic agonists have been developed.

RXR (retinoid X receptor) belongs to the nuclear receptor superfamily, and as with RAR, retinoic acid and other ligands regulate its transcriptional activity. The RXR forms heterodimers with various nuclear receptors, including RARs, and regulates the transcriptional activity of its partner nuclear receptors in a complex manner through binding to specific nucleotide sequences and recruitment of transcription-coupling factors.

The term "in the presence of a RAR agonist or an RXR agonist" means under a culture condition capable of activating RAR or RXR, and the means thereof is not particularly limited, and any means capable of activating RAR or RXR can be used. Substances that act directly on RAR or RXR to operate its function, agents that promote expression of RAR or RXR itself, or the like can be used in the present invention. It can also control the functions of transcription factors or transcription coupling factors that interact with RAR or RXR, and RAR or RXR by regulating their expression and post-translational modifications, etc.

Although not particularly limited in the present invention, as the RAR agonist or the RXR agonist, for example, the following compounds can be used. Preferably, TTNPB, retinoic acid, CH55, AM580 can be used.

TTNPB (arotinoidal acid, CAS No.: 71441-28-6)

[Chemical 8]

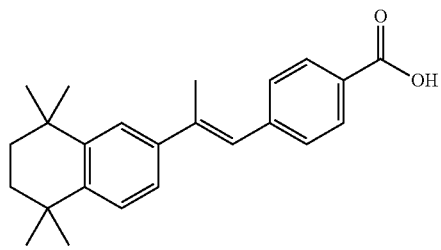

Retinoic acid (CAS No.: 302-79-4)
Tretinoin (CAS No.: 302-79-4)

Adapalene (CAS No.: 106685-40-9)

Bexarotene (CAS No.: 153559-49-0)

Tazarotene (CAS No.: 118292-40-3)

Tamibarotene (CAS No.: 94497-51-5)

CH55 (CAS No.: 110368-33-7)

AM580 (CAS No.: 102121-60-8)

The concentration of the RAR agonist or the RXR agonist may be appropriately determined, and is not particularly limited, and may be used, for example, in the range of 0.05 µmol/L to 10 µmol/L, preferably 0.5 µmol/L to 5 µmol/L.

1.2.7 PDK1 Activators

PDK1 (phosphoinositide-dependent protein kinase-1) is a phosphorylating enzyme that phosphorylates and activates AKTs and functions as a center of the inositol phospholipid-mediated signaling pathway. This PDK1/AKT signal pathway plays crucial roles in cellular viability, proliferation, carbohydrate and lipid metabolisms, etc. PS48, a PDK1 activator, binds directly to PDK1 and phosphorylates AKTs to activate this signal pathway.

The term "in the presence of a PDK1 activator" means under a culture condition capable of activating PDK1, and the means thereof is not particularly limited, and any means capable of increasing intracellular PDK1 concentrations, for example, can be used. Since PDK1 is activated by phosphatidylinositol-3 phosphate, which is produced by activation of phosphoinositide-3 kinase (PI3K) through various receptors, including tyrosine kinase receptors, cytokine receptors, and G protein-coupled receptors, substances that activate these receptors or other stimuli that induce the production of phosphatidylinositol-3 phosphate can also be a means to activate PDK1.

As the PDK1 activator, for example, the following compounds can be used. Preferably, PS48 can be used.

PS48 ((2Z)-5-(4-Chlorophenyl)-3-phenyl-2-pentenoic acid, CAS No.: 1180676-32-7)

OSU-03012 (AR-12) (CAS No.: 742112-33-0)

BX795 (CAS No.: 702675-74-9)

BX912 (CAS No.: 702674-56-4)

PHT-427 (CAS No.: 1191951-57-1)

The concentration of the PDK1 activator may be appropriately determined, and is not particularly limited, and may be, for example, in the range of 0.5 µmol/L to 30 µmol/L, preferably 1 µmol/L to 10 µmol/L.

1.2.8 ERK Inhibitors

ERK (Extracellular Signal-regulated Kinase) is a subfamily of EGF (Epidermal Growth Factor), MAPK that is activated by serum-stimulating or oxidative stress, etc., and ERK is divided into ERK1/2, ERK5, ERK7, ERK8 by differences in the signal transduction pathways involved. Ligand-binding to tyrosine kinase receptors, such as the epidermal growth factor receptor (EGFR), results in signal flow, which phosphorylates and activates TEY-motifs present in the activation loops of ERK.

The term "in the presence of an ERK inhibitor" means under a culture condition capable of inhibiting ERK, and the means thereof is not particularly limited, and substances which inhibit the activity of ERK, for example, an ERK signal inhibition means such as an anti-ERK antibody or an ERK inhibitor can be used. Means for inhibiting enzymes involved in ERK activation, such as ERK kinase and ERK kinase kinase, can also be used for ERK inhibition.

Although not particularly limited in the present invention, as the ERK inhibitor, the following compounds can be used. Preferably, GDC-0994 (Ravoxertinib) can be used.
GDC-0994 (CAS No.: 1453848-26-4)

[Chemical 9]

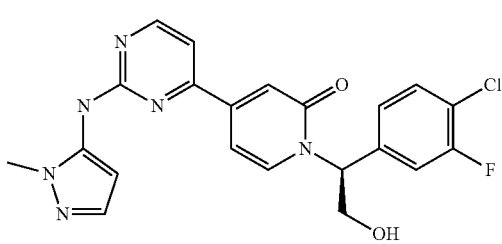

SCH772984 (CAS No.: 942183-80-4)
MK-8353 (SCH900353) (CAS No.: 1184173-73-6)
Magnolin (CAS No.: 31008-18-1)
LY3214996 (CAS No.: 1951483-29-6)
FR 180204 (CAS No.: 865362-74-9)
AZD0364 (CAS No.: 2097416-76-5)

The concentration of the ERK inhibitor may be appropriately determined, and is not particularly limited, and may be used, for example, in the range of 0.1 µmol/L to 10 µmol/L, preferably 0.2 µmol/L to 5 µmol/L.

1.3 Somatic Cell Culture

The cultivation of the somatic cells in the present invention process may be carried out in the presence of various inhibitors (and, optionally, inducers or activating agents) described above by selecting the culture medium, temperature, and other conditions according to the type of somatic cells used. The medium can be selected from known media or commercially available media. For example, MEM (Minimum Essential Medium), DMEM (Dulbecco's Modified Eagle Medium), DMEM/F12, or a medium obtained by modifying MEM (Minimum Essential Medium), DMEM (Dulbecco's Modified Eagle Medium), which is a common medium, can be used by adding appropriate components (sera, proteins, amino acids, sugars, vitamins, fatty acids, antibiotics, and the like).

As the culture conditions, general cell culture conditions may be selected. Conditions such as 37° C. and 5% $CO_2$ are illustrated. It is preferred to change the medium at appropriate intervals during culture, preferably once every 1 to 7 days, more preferably once every 3 to 4 days. When the present invention process is carried out using fibroblasts as materials, cardiomyocytes appear in 5 to 8 days to 3 weeks at 37° C. and 5% $CO_2$. It is also possible to convert somatic cells, the number of which has been increased in advance, into cardiomyocytes by selecting somatic cells which can be easily cultured as the somatic cells to be used. Thus, the production of scaled-up cardiomyocytes is also easy.

Cell culture vessels such as plates, dishes, cell culture flasks, cell culture bags, and the like can be used for culturing somatic cells. As the cell culture bag, a bag having gas permeability is suitable. If large quantities of cells are required, a large culture vessel may be used. Culturing can be carried out either in an open system or in a closed system, but when administration of the obtained cardiomyocyte to a human or the like is intended, it is preferable to carry out culturing in a closed system.

In the present invention process, by culturing somatic cells in a medium containing various inhibitors and the like described above, it is possible to produce cardiomyocytes from somatic cells by one step of culturing.

In the present invention process, cardiomyocytes are produced from somatic cells. 5-Azacytidine, angiotensin II, BMP-2 (Bone Morphogenetic Protein 2), dimethyl sulfoxide (DMSO), and the like are known to be useful agents for induction differentiation into cardiomyocytes. As an effective substance for induction differentiation into cardiomyocytes, for example, a substance commercially available as a differentiation inducing agent can be used. In the present invention, somatic cells can be cultured in the presence of the substance described above.

1.4 Cardiomyocytes

The cell population containing cardiomyocytes can be obtained by the above-described present invention process. The cardiomyocytes produced by the present invention process are also within the scope of the present invention. The cardiomyocytes produced by the present invention process may be a progenitor cell destined to differentiate into a cardiomyocyte in addition to a terminally differentiated cell.

The cardiomyocytes produced by the present invention process are so-called low molecular weight chemical compound-induced cardiomyocytes (ciCMs), which are derived directly from somatic cells by small molecule compounds, and are distinguished from cardiomyocytes derived from ES cells and iPS cells. Further, a difference in the low molecular weight compounds used distinguishes them from the low molecular weight compound-induced cardiomyocytes described in Patent Document 1 and the like.

The cardiomyocytes produced by the present invention process can be detected, confirmed, and separated using, for example, morphological changes of the cells, characteristic properties of the cardiomyocytes, and specific markers.

Cardiomyocytes have features, not present in other cells, of beating autonomously and can be distinguished from other cells by microscopic observation. Specific markers of cardiomyocytes include, but are not limited to, cardiomyotroponin C (cTnT), a myosin heavy chain, a actin, and the like.

Quarantine methods (detection by antibodies) can be used for detection of specific markers, but detection of protein molecules may be carried out by quantitation of mRNA amount of protein molecules. Antibodies that recognize specific markers of cardiomyocytes are also useful for isolating and purifying cardiomyocytes obtained by the present invention process.

The cardiomyocytes produced by the present invention process can be used, for example, for tissue repair and the like. The cardiomyocytes produced by the present invention process can be used to produce pharmaceutical compositions for tissue repair and the like. As a means for treating heart disease such as heart failure or myocardial infarction, a method for manufacturing cardiac myocytes and a method for transplanting cardiac myocytes have been developed. For example, a myocardial sheet formed by stacking cardiomyocytes, endothelial cells, and the like exhibits excellent therapeutic effects and engraftment properties, so that it is expected to be used for the treatment of severe heart failure.

When the cardiomyocytes produced by the present invention process is used as a pharmaceutical composition, the cardiomyocytes may be mixed with a pharmaceutically acceptable carrier by a conventional method to prepare a formulation in a form suitable for administration to an individual. Carriers include, for example, saline, distilled water for injection made isotonic with glucose and other adjuvants (e.g., D-sorbitol, D-mannitol, sodium chloride, etc.). In addition, buffers (e.g., phosphate buffer, sodium acetate buffer), analgesics (e.g., benzalkonium chloride, procaine hydrochloride, etc.), stabilizers (e.g., human serum albumin, polyethylene glycol, etc.), preservatives, antioxidants, and the like may be included.

The cardiomyocytes produced by the present invention process may further be a composition in combination with other cells or components effective for the functional exertion or the improvement of the engraftment of the cardiomyocytes.

Furthermore, the cardiomyocytes produced by the present invention process can be used for screening a drug candidate compound acting on the cardiomyocytes or for safety evaluation of the drug candidate compound. The cardiomyocytes are an important tool for assessing the cardiotoxicity of drug candidates. According to the present invention process, since a large number of cardiomyocytes can be obtained by one operation, it is possible to obtain a reproducible research result without being affected by a lot difference of cells.

2 Composition

The composition according to the present invention (hereinafter referred to as the "composition of the present invention") is a composition for producing a cardiomyocyte by inducing differentiation directly from a somatic cell, and is characterized by comprising a MEK-inhibitor.

The composition of the present invention can preferably include one that comprises a cAMP inducer. More preferably, the composition of the present invention can include one that further comprises at least one member selected from the group consisting of a TGF-β inhibitor, a PDE4 inhibitor, and a GR agonist. Still more preferably, the composition of the present invention can include one that further comprises an ERK inhibitor.

Particularly preferred is the composition of the present invention which comprises any combination of the following (1) to (6);
 (1) a MEK inhibitor, a cAMP inducer, and a TGF-β inhibitor,
 (2) a MEK inhibitor, a cAMP inducer, and a PDE4 inhibitor,
 (3) a MEK inhibitor, a cAMP inducer, and a GR agonist,
 (4) a MEK inhibitor, a cAMP inducer, a PDE4 inhibitor, and a GR-agonist,
 (5) a MEK inhibitor, a cAMP inducer, a TGF-β inhibitor, a PDE4 inhibitor, and a GR agonist,
 (6) a MEK inhibitor, a cAMP inducer, a TGF-β inhibitor, a PDE4 inhibitor, a GR agonist, and an ERK inhibitor.

The present invention also includes a composition for producing a cardiomyocyte by inducing differentiation directly from a somatic cell, characterized by comprising a cAMP inducer, a TGF-β inhibitor, a PDE4 inhibitor, a GR agonist, and an ERK inhibitor. Hereinafter, such a composition is also referred to as the composition of the present invention.

The composition of the present invention can further comprise at least one member selected from the group consisting of a RAR agonist, an RXR agonist, and a PDK1 activator.

The composition of the present invention may comprise at least any combination of the above, and may optionally further comprise other inhibitors, inducing agents, and the like.

Each of the above inhibitors, inducers, and the like may be alone or a combination of two or more kinds.

Specific inhibitors and the like may have two or more kinds of inhibitory effects, and in this case, one inhibitor and the like may be considered to include a plurality of inhibitors and the like.

Specific examples and preferable examples of the inhibitor, the inducer, and the like described above are the same as those described above.

The composition of the present invention can be used as a composition for producing a cardiomyocyte from a somatic cell. The composition of the present invention can also be used as a medium for producing a cardiomyocyte from a somatic cell.

Examples of the medium used for the production of a cardiomyocyte from a somatic cell include a basal medium produced by mixing components required for cell culture, and a medium containing a MEK inhibitor, a cAMP inducer, and the like as active ingredients. The above-mentioned active ingredient may be contained in a concentration effective for the production of a cardiomyocyte, and the concentration can be appropriately determined by a skilled person in the art. Basal media can be selected from known media or commercially available media. For example, MEM (Minimum Essential Medium), DMEM (Dulbecco's Modified Eagle Medium), DMEM/F12, or a medium modified with these, which are conventional mediums, can be used as the base medium.

The medium may further be supplemented with known medium components as described hereinabove, such as serum, proteins such as albumin, transferrin, growth factors, etc., amino acids, sugars, vitamins, fatty acids, antibiotics, etc.

The medium may further be supplemented with a substance effective to induce differentiation into cardiomyocytes, as described hereinabove.

Furthermore, in the present invention, a MEK inhibitor, a cAMP inducer, and the like can be administered to a living body to produce a cardiomyocyte from a somatic cell in the living body. That is, the present invention provides a process for producing a cardiomyocyte from a somatic cell in vivo, comprising administering a MEK inhibitor, a cAMP inducer, and the like to a living organism. Preferred combinations of inhibitors and the like for administration to an organism are as described herein. Examples of the living body include humans, mammals other than humans, and animals other than mammals (birds, reptiles, amphibians, fish, etc.), but humans are particularly preferable. By administering a MEK inhibitor, a cAMP inducer, and the like to a specific site in a living body, a cardiomyocyte can be produced from a somatic cell at the specific site.

EXAMPLE

Hereinafter, the present invention will be illustrated in detail by examples and test examples, but the present invention is not limited to the ranges described in the examples and the like.

Example: Production of Cardiomyocytes

<Direct Induction from Human Fibroblasts to Cardiomyocytes>
(1) Human Fibroblasts The human fibroblasts used as the material were purchased from DS Pharma Biomedical Co., Ltd. The fibroblasts are derived from 38-year-old human skin.

(2) Direct Induction from Human Fibroblasts to Cardiomyocytes.

The human fibroblasts were seeded in 8×10⁴ portions in 35-mm dishes coated with gelatin (Cat #: 190-15805, manufactured by Wako Pure Chemical Co.) and cultured in DMEM high glucose medium (manufactured by Gibco) supplemented with 10% fetal bovine serum (Fetal bovine serum; FBS), 100 U/mL penicillin, and 100 µg/mL streptomycin for 2 days at 37° C. under 5% $CO_2$ conditions (80-90% or more confluent). DMEM denotes Dulbecco's Modified Eagle Medium (Dulbecco's Modified Eagle Medium).

The medium of dishes of the human fibroblasts described above was replaced with a medium of DMEM (High Glucose with L-Glutamine Phenol Red, and Sodium Pyruvate) (manufactured by Gibco) having 20% fetal bovine serum (FBS), 2% B27-supplement (manufactured by Gibco), 1% N2 (manufactured by Gibco), non-essential amino acids (NEAA: manufactured by Gibco), β-mercaptoethanol (manufactured by Nacalai Tesque; final concentration of 0.1 mmol/L), 2-phospho ascorbic acid (manufactured by Sigma-Aldrich; final concentration of 50 µg/mL), 100 U/mL penicillin, 100 µg/mL streptomycin, and low molecular weight compounds described below. After that, the culture medium was changed every three days to the culture medium having the same composition, and the culture medium was cultured at 37° C. under 5% $CO_2$ conditions.

<Low Molecular Weight Compounds>
2 µM PD0325901 (Cat #: 162-25293, Wako)
15 µM forskolin (Cat #: 063-02193, Wako)
5 µM RepSox (Cat #: 1894-25, BioVision)
3 µM rolipram (Cat #: 180-01411, Wako)
dexamethasone (Cat #: 047-18863, Wako)
retinoic acid (Cat #: 186-01114, Wako)
2 µM TTNPB (Cat #: 16144, Cayman Chemical)
100⁴ PS48 (Cat #:164-25011, Wako)

(3) Results

The results of culturing according to the above (2) are shown in Tables 1 and 2 and FIGS. 1 to 6. In the table, "+" indicates the presence of the compound in the medium, and "−" indicates the absence of the compound in the medium.

TABLE 1

| Chemical compound | function | Ex. 1 | Ex. 2 | Ex. 3 | Ex. 4 | Ex. 5 | Ex. 6 | Comp. Ex. 1 |
|---|---|---|---|---|---|---|---|---|
| PD0325901 | MEK inhibitor | + | + | + | + | + | + | − |
| Forskolin | cAMP inducer | + | + | + | + | + | + | + |
| RepSox | TGF-β inhibitor | + | − | + | + | + | + | + |
| Rolipram | PDE4 inhibitor | + | + | − | + | + | + | + |
| Dexamethasone | GR agonist | + | + | + | − | + | + | + |
| Retinoic acid | RAR agonist | + | + | + | + | − | + | + |
| TTNPB | RAR, RXR agonist | + | + | + | + | − | + | + |
| PS48 | PDK1 activator | + | + | + | + | + | − | + |
| Induction efficiency | Morphology, pulsation | ◎ | ○ | ○ | Δ | ○ | ◎ | X |

TABLE 2

| Chemical compound | function | Comp. Ex. 2 | Ex. A | Ex. 7 | Ex. 8 | Ex. 9 | Ex. 10 | Ex. 11 | Ex. 12 |
|---|---|---|---|---|---|---|---|---|---|
| PD0325901 | MEK inhibitor | − | + | + | + | + | + | + | + |
| Forskolin | cAMP inducer | + | − | + | + | + | + | + | + |
| RepSox | TGF-β inhibitor | − | − | − | + | − | − | − | + |
| Rolipram | PDE4 inhibitor | − | − | − | − | + | − | + | + |
| Dexamethasone | GR agonist | − | − | − | − | − | + | + | + |
| Induction efficiency | Morphology, pulsation | X | Δ | ○ | ○ | ○ | ○ | ◎ | ○ |

(4) Evaluation of Cardiomyocytes

In the experiment, myocardial-like cells appeared from about the 5$^{th}$ day after culturing with adding low molecular weight compounds. This was assessed by observing cell clumps that contract spontaneously and periodically under a microscope. The photographs of cells (FIGS. 1-6) were taken, the 7$^{th}$ day and the 10$^{th}$ day (FIGS. 1-3), the 7$^{th}$ day and the 13$^{th}$ day (FIGS. 4 and 5), or the 13$^{th}$ day and the 17$^{th}$ day (FIG. 6) after culturing with adding low molecular weight compounds, respectively.

In addition, for some of the combinations of low molecular weight compounds in Table 2, the low molecular weight compounds were added to extract total RNA from the cells after 17 days of culturing, and the expression amounts of the cardiomyocyte-specific gene Tbx1 and the cardiomyocyte-specific gene Tnnt2 were quantified by real-time PCR. The results are shown in FIG. 7. Tbp in the drawing denotes a gene serving as an internal standard, and mRNA amounts of Tbx1 and Tnnt2 are evaluated based on the relative values based on mRNA amounts. The combination compounds of the symbols in the drawing are as follows.
C: Control (without applicable low molecular weight compound)
M: Example A
F: Comparative Example 2
MF: Example 7
MF+Rep: Example 8
MF+Roli: Example 9
MF+Dex: Example 10
MF+Rep+Roli+Dex: Example 12

As is evident from Table 1 and the photographs in FIGS. 1-3, the removal of PD0325901 (MEK-inhibitor) from combinations of compounds, in particular, resulted in few spontaneously shrinking clumps of cells. As is clear from Table 2 and the photographs in FIGS. 4-6, myocardial clumps of cells appeared by adding PD0325901 (MEK inhibitor) and forskolin (cAMP inducer) or only PD0325901 (MEK inhibitor) although low in frequency. As shown in the photograph of FIG. 6, it was confirmed that cell clumps that move spontaneously were generated not only in one place but also in a plurality of places.

From FIG. 7, it was found that the gene specific for the cardiomyocyte was activated by the combination of the respective compounds as compared with the expression level of the cell when the low molecular weight compound was not added. In particular, the combination of three compounds (PD0325901 (MEK inhibitor), forskolin (cAMP inducer), RepSox (TGF-β)) and five compounds (PD0325901 (MEK inhibitor), forskolin (cAMP inducer), RepSox (TGF-β), rolipram (PDE4 inhibitor), dexamethasone (GR agonist)) greatly increased the expression of both of these genes.

The experimental results indicate that MEK inhibitors are critical compounds for the induction of cardiomyocytes, and that culturing them at least in the presence of MEK inhibitors (e.g., PD0325901) or cAMP inducers (e.g., forskolin) results in cardiomyocytes with good induction efficiencies. Expression of the particular genes was also prominent when cultured in the presence of MEK inhibitors and cAMP inducers, as well as TGF-β inhibitors, PDE4 inhibitors, and GR agonists.

Test Example 1

(1) Cardiomyocyte Gene Expression

Cell cultures were carried out in the same manner as in the above Examples by adding four compounds (4C) of PD0325901 (MEK inhibitor), forskolin (cAMP inducer), RepSox (TGF-β), and rolipram (PDE4 inhibitor), or five compounds having dexamethasone (GR agonist) in addition to these compounds, total RNA was extracted from cells after 18 days of culture, and the expression levels of cardiomyocyte progenitor cell specific genes Hand2 and Tbx1, cardiomyocyte specific gene Tnnt2, Nppa, and Nkx2.5 were quantified by real-time PCR. The results are shown in FIG. 8. Tbp in the drawing indicates a gene as an internal standard, and mRNA amount of each gene is evaluated based on the relative value based on mRNA amount of the internal standard. In the drawing, "No compound" indicates the result when no said compound is added, and "4C+Dex" indicates the result when all of the above five compounds are added.

As is clear from FIG. 8, it was shown that direct induction from human skin fibroblasts to cardiomyocytes proceeded by culturing with 4C or a group of compounds to which dexamethasone (GR agonist) was added.

(2) Immunostaining

In the above (1), cells cultured by adding a compound group in which dexamethasone (GR agonist) was added to 4C were fixed with 4% paraformaldehyde the 18$^{th}$ day after culturing, and then immunostained. Anti Sarcomeric Alpha Actinin antibodies (ab9465, Abcam; used at 200-fold dilutions) were used for staining. The results are shown in FIG. 9. In the drawing, red indicates Alpha Actinin staining, and blue indicates nuclear staining with DAPI (4',6-diamidino-2-phenylindole). Since FIG. 9 is displayed in gray, red, blue, and the like are not illustrated, but in an actual original photograph, red, blue, and the like are illustrated.

As shown in FIG. 9, after adding the said compound group and culturing, Alpha Actinin staining was observed in a certain number of cardiomyocytes, and staining was observed relatively in the cytoplasm rather than in the cell nuclei stained with DAPI. Expression of Alpha Actinin, a marker of cardiomyocytes, was observed in some cells, and immunostaining results also showed that direct induction from human dermal fibroblasts to cardiomyocytes was promoted by culturing the said compound group.

Test Example 2

The cell culture was carried out in the same manner as in the above examples by adding the following low molecular weight compound combinations. The state of the cells on the 13$^{th}$ and 19$^{th}$ days after culturing with adding the compound group is shown in FIG. 10.

In FIG. 10, "5C" represents a combination of five kinds of compounds other than Trametinib among the six kinds of low molecular weight compounds described below, and the left two photographs show the culture results of adding the compound group. "5C-M" represents a group of compounds removing PD0325901 (MEK inhibitor) from the group of 5C compounds, and the two photographs in the middle show the culture results of adding the group of compounds. "5C-M+Trametinib" represents a group of compounds removing PD0325901 (MEK inhibitor) from the group of 5C compounds and adding Trametinib, which is another MEK inhibitor, and the two photographs on the right show the culture results of adding the compounds.

<Low Molecular Weight Compounds>
2 μM PD0325901 (Cat #: 162-25293, Wako)
15 μM forskolin (Cat #: 063-02193, Wako)
5 μM RepSox (Cat #: 1894-25, BioVision)
3 μM rolipram (Cat #: 180-01411, Wako)
1 μM dexamethasone (Cat #: 047-18863, Wako)
3 μM Trametinib (Cat #: HY-10999, MedChem Express)

As is clear from FIG. 10, it was shown that MEK inhibitors are important for direct induction from human skin fibroblasts to cardiomyocytes.

Test Example 3

The combinations of the following low molecular weight compounds were added and culturing was conducted in the same manner as in the above examples. The state of the cells on the 7$^{th}$ and 12$^{th}$ days after culturing with adding the low molecular weight compounds is shown in FIG. 11.

In FIG. 11, "5C" represents a combination of five kinds of compounds other than GDC-0994 among the six kinds of low molecular weight compounds described below, and the two photographs at the left end indicate the culture results of adding the compound group. "5C-M" represents a group of compounds removing PD0325901 (MEK inhibitor) from the group of 5C compounds, and the second two photographs from the left show the culture results of adding the group of compounds. "5C-M+GDC-0994" represents a group of compounds in which PD0325901 (MEK inhibitor) is removed from the group of 5C compounds and GDC-0994 (ERK inhibitor) is added instead, and the second two photographs from the right show the culture results of adding the group of compounds. "5C+GDC-0994" represents a group of compounds adding GDC-0994 (an ERK inhibitor) to the group of 5C compounds, and the two photographs at the right end indicate the culture results of adding the group of compounds.

<Low Molecular Weight Compounds>
PD0325901 (Cat #: 162-25293, Wako)
15 μM forskolin (Cat #: 063-02193, Wako)
5 μM RepSox (Cat #: 1894-25, BioVision)
rolipram (Cat #: 180-01411, Wako)
dexamethasone (Cat #: 047-18863, Wako)
GDC-0994 (Cat #: 21107, Cayman Chemical)

As shown in FIG. 11, direct induction from human skin fibroblasts to cardiomyocytes was possible if ERK inhibitors were present even in the absence of MEK inhibitors. We also found that the presence of both MEK and ERK inhibitors promoted direct induction from human skin fibroblasts to cardiomyocytes.

The invention claimed is:

1. A process for producing a myocardial-like cell, comprising a step of culturing a fibroblast as a starting material in the presence of a MEK inhibitor, a cAMP inducer, a PDE4 inhibitor, and a GR agonist, or in the presence of a MEK inhibitor, a cAMP inducer, a PDE4 inhibitor, a TGF β inhibitor, and a GR agonist under a basal medium supplemented by at least one member selected from the group consisting of serum, a protein, an amino acid, a sugar, a vitamin, a fatty acid, and an antibiotic, and culture conditions for directly inducing differentiation of a fibroblast into a myocardial-like cell, wherein a myocardial-like cell is produced.

2. The process for producing a myocardial-like cell according to claim 1, wherein the said step is a step of culturing a fibroblast as a starting material in the further presence of an ERK inhibitor.

3. The process for producing a myocardial-like cell according to claim 1, wherein the said step is a step of culturing a fibroblast as a starting material in the presence of any of the following combinations (1) to (2);
   (1) a MEK inhibitor, a GR agonist, a cAMP inducer, and a PDE4 inhibitor, and an ERK inhibitor,
   (2) a MEK inhibitor, a cAMP inducer, a TGF-β inhibitor, a PDE4 inhibitor, a GR agonist, and an ERK inhibitor.

4. The process for producing a myocardial-like cell according to claim 1, wherein the said step is a step of culturing a fibroblast as a starting material in the further presence of at least one member selected from the group consisting of a RAR agonist, an RXR agonist, and a PDKI activator.

5. The process for producing a myocardial-like cell, according to claim 1, wherein the MEK inhibitor is PD0325901 or trametinib.

6. The process for producing a myocardial-like cell according to claim 1, wherein the cAMP inducer is forskolin.

7. The process for producing a myocardial-like cell according to claim 1, wherein the TGF-β inhibitor is RepSox, the PDE4 inhibitor is rolipram, or the GR agonist is dexamethasone.

8. The process for producing a myocardial-like cell according to claim 2, wherein the ERK inhibitor is GDC-0994.

* * * * *